United States Patent
Eckerdal et al.

(10) Patent No.: US 7,242,980 B2
(45) Date of Patent: Jul. 10, 2007

(54) IMPLANTABLE HEART STIMULATOR WITH INFECTION CONTROL CURRENT, EMPLOYING COUNTER ELECTRODE

(75) Inventors: Johan Eckerdal, Bromma (SE); Martin Obel, Danderyd (SE); Eva Micski, Huddinge (SE)

(73) Assignee: St. Jude Medical AB, Jarfalla (SE)

( * ) Notice: Subject to any disclaimer, the term of this patent is extended or adjusted under 35 U.S.C. 154(b) by 507 days.

(21) Appl. No.: 10/468,589

(22) PCT Filed: Feb. 26, 2002

(86) PCT No.: PCT/SE02/00346

§ 371 (c)(1),
(2), (4) Date: Aug. 20, 2003

(87) PCT Pub. No.: WO02/068043

PCT Pub. Date: Sep. 6, 2002

(65) Prior Publication Data

US 2004/0093036 A1    May 13, 2004

(30) Foreign Application Priority Data

Feb. 27, 2001  (SE) .................................. 0100661

(51) Int. Cl.
*A61N 1/05* (2006.01)
(52) U.S. Cl. .............. 607/9; 607/36; 604/265
(58) Field of Classification Search ................. 607/9, 607/36; 604/265
See application file for complete search history.

(56) References Cited

U.S. PATENT DOCUMENTS 3,942,535 A * 3/1976 Schulman .................... 607/33
4,886,505 A 12/1989 Haynes et al.
5,312,813 A 5/1994 Costerton et al.
5,409,467 A 4/1995 Raad et al.
5,462,644 A 10/1995 Woodson (Continued)

OTHER PUBLICATIONS

"Prevention and Control of Bacterial Infections Associated with Medical Devices," Khoury et al., ASAIO Journal, 1992, pp. M174-M178.

(Continued)

*Primary Examiner*—Carl Layno
*Assistant Examiner*—Deborah Malamud
(74) *Attorney, Agent, or Firm*—Schiff Hardin LLP

(57) ABSTRACT

An implantable heart stimulator has a pulse generator, implantable in a subcutaneous pocket, and an electrode lead connected thereto for delivering stimulation pulses to a patient's heart. The pulse generator has an electrically conductive housing, and the electrode lead has a proximal portion which after implantation, extends substantially from the housing to a location situated beyond entry into the venous system and before entry into the superior vena cava. The proximal portion has an exterior with an electrically conductive surface, which together with the housing, form an infection control current electrode. A counter electrode is disposed outside of the subcutaneous pocket, and a current source supplies an infection control current between the infection control current electrode and the counter electrode for counteracting bacterial growth at least on an exterior of the housing.

23 Claims, 2 Drawing Sheets

U.S. PATENT DOCUMENTS

| | | |
|---|---|---|
| 5,510,766 A | 4/1996 | Harman et al. |
| 5,713,926 A | 2/1998 | Hauser et al. |
| 5,814,076 A | 9/1998 | Brownlee |
| 6,258,249 B1 | 7/2001 | Simpson |
| 6,282,444 B1 | 8/2001 | Kroll et al. |
| 6,493,586 B1 * | 12/2002 | Stahmann et al. ............ 607/27 |

OTHER PUBLICATIONS

"Mechanism of Electrical Enhancement of Efficacy of Antibiotics in Killing Biofilm Bacteria," Costerton et al., Antimicrobial Agents and Chemotherapy, Dec. 1994, pp. 2803-2909.

* cited by examiner

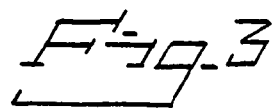
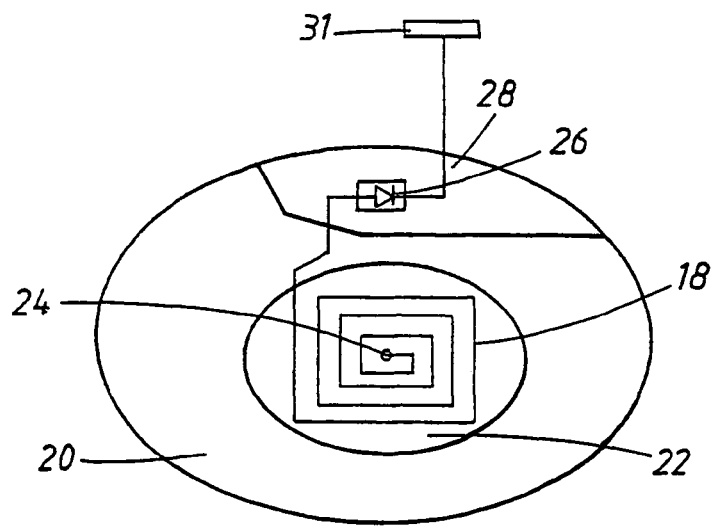
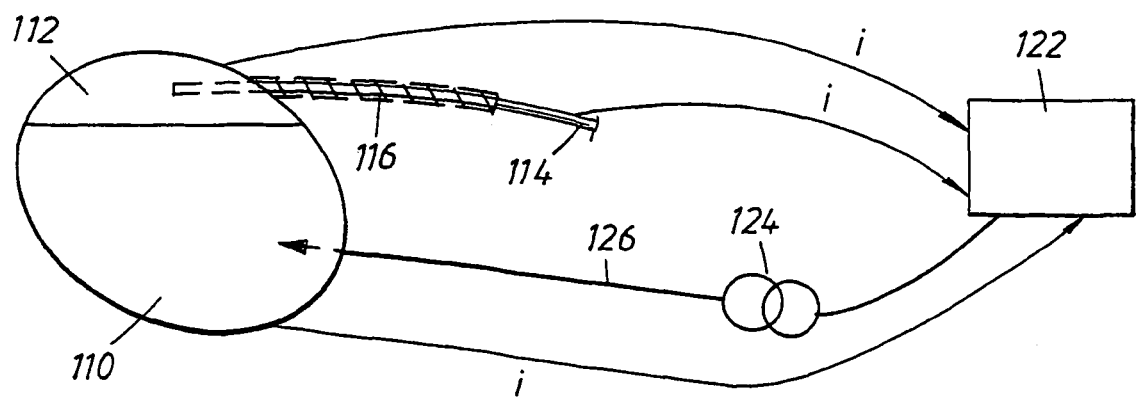

IMPLANTABLE HEART STIMULATOR WITH INFECTION CONTROL CURRENT, EMPLOYING COUNTER ELECTRODE

BACKGROUND OF THE INVENTION

1. Field of the Invention

The present invention relates to an infection control apparatus for an implantable heart stimulator of the type having a pulse generator for delivering electric stimulation pulses to a patient's heart through a lead connectable to the pulse generator the pulse generator housing being electrically conductive.

2. Description of the Prior Art

Implantable heart stimulator pocket infection is a severe complication which often ends up in explanation of the stimulator. The reason therefor is that conventional treatment with antibiotics cannot eradicate the infection. This seems to depend on the circumstance that the bacteria live in a biofilm formed around the exterior surfaces of the implanted stimulator, which film blocks antibiotics. The bacteria may also live passively on a very low metabolism and can therefore not be treated successfully by antibiotics.

A method of enhancing the effect of antibiotics by applying an electrical field across the biofilm is described in U.S. Pat. No. 5,312,813. This method is based on findings by J. W. Costerton et.al. Their studies have shown that the infection can be completely cured and no explanation has to take place by applying an electric field or a small current across the biofilm during antibiotic treatment, cf. also ASAIO Journal 1992, p.M-174 M178, Khoury et.al, "Prevention and Control of Bacterial Infections Associated with Medical Devices", and Antimicrobial Agents and Chemotherapy, Vol. 38, No. 12, December 1994, p. 2803-2809, Costerton et.al., "Mechanism of Electrical Enhancement of Efficacy of Antibiotics in Killing Biofilm Bacteria" In these studies, generally, a low electric current of the order of 15-400 $\mu A/cm^2$ is applied onto the infected surface while immersed in a buffer with antibiotics. In the most successful studies a total killing of microorganisms was reported after only 8 hours of current and antibiotic treatment—tobramycin 2.5 mg/l, 15-400 $\mu A/cm^2$ during 8 h. This effect has been termed "the bioelectric effect".

These studies suggest that the electric field needs to be applied in close proximity to the infected implant. A passive electric field will not be effective, but a current should be conducted between electrodes in the biofluid surrounding the implanted device. A possible explanation to the observed effect is that electrochemically generated products are needed for the bioelectric effect to occur. At the titanium surface, titanium being normally used in heart stimulator housings, the following electrochemical processes take place.

At the anode:
1) $2H_2O \rightarrow O_2 + 4H^+ + 4e^-$
2) $2Cl^- \rightarrow Cl_2 + 2e^-$
3) $Ti + 2H_2O \rightarrow TiO_2 + 4H^+ + 4e^-$ At the cathode:
1) $O_2 + 2H_2O + 4e^- \rightarrow 4OH^-$
2) $2H_2O + 2e^- \rightarrow H_2 + 2OH^-$ It is supposed that primarily the produced oxygen and chloride gases have an influence on the biofilm attached to the surface. It is also supposed that the fact that the pH-value is towered at the anode and increased at the cathode is significant for the influence and viability of the biofilm.

An infection that is initiated in the stimulator pocket will also often start to spread along the lead. The polymer surface of the lead may be a substrate for the bacteria and makes it easy for the bacteria to attach. At the time when a pocket infection is clinically manifested, in many cases the infection has already spread some distance from the stimulator pocket along the lead.

SUMMARY OF THE INVENTION

Since the bioelectric effect is concentrated to parts in conjunction with or in close proximity to conducting surfaces of the implant, it is an object of the present invention to extend these conducting active surfaces to practically the whole exterior surface of the implant, such that it can be current permeated.

The above object is achieved in accordance with the principles of the present invention in an implantable heart stimulator having a pulse generator, adapted for implantation in a subcutaneous pocket, and an electrode lead connected thereto for delivering stimulation pulses to the heart of a patient, the pulse generator having an electrically-conductive housing, an electrode lead having a proximal portion which, after implantation, extends substantially from the housing to a location situated beyond entry of the electrode lead into the venous system and before entry of the electrode lead into the superior vena cava, the proximal; portion having an exterior with an electrically conductive surface and the housing and this electrically conductive surface forming an infection control current electrode, a counter electrode disposed outside of the subcutaneous pocket, and a current source for supplying an infection control current between the infection control current electrode and the counter electrode, for counteracting bacterial growth at least on an exterior of the housing.

As discussed above the bioelectric effect is limited to conducting surfaces of the implanted device or to the immediate proximity thereof. With the present invention a design is obtained which makes it possible to extend the bioelectric effect to surfaces of an implanted heart stimulator that are conventionally non-conducting. Such devices can be a pacemaker or a cardioverter—defibrillator (ICD). By making also exterior surfaces of the proximal part of the lead and the connector top (if present) electrically conductive all exterior stimulator surfaces located within the subcutaneous implant pocket and a part of the lead extending from the pocket are electrically conductive, and by adapting these electrically conductive surfaces to form at least two separate electrodes, and providing a current source to supply an electric infection control current between these electrodes all exterior surfaces will be permeated by current, and the bioelectric effect will be extended to all surfaces within the pocket and also to the exterior surface of the proximal part of the lead. By making the normally non-conducting surfaces of the connector top (if present) and the lead electrically conducting, not only is effective treatment of infections within the pocket possible, but also spreading of the infection from the pocket along the lead is prevented. The lead will in this way benefit from the bioelectric effect and thus bacteria are prevented from reaching the endocardium giving rise to endocarditis.

In an advantageous embodiment of the apparatus according to the invention an electrically conducting polymer is applied on the exterior surfaces of the proximal part of the lead and the connector top (if present). In this way conventionally non-conducting surfaces of a heart stimulator are made electrically conductive. An example of a polymer suitable for this purpose is an electrically conducting polymer marketed under the trademark ELASTOSIL.

In another embodiment of the apparatus according to the invention an electrically conducting coil is applied around the proximal part of the lead. In this way the proximal part of the lead is made not only electrically conductive but also the wear resistance of the lead is improved.

In another embodiment of the apparatus according to the invention the exterior surfaces of the proximal part of the lead and of said connector top (if present) are treated by ion implantation technology or so-called Ion-Beam-Assisted-Deposition. This technique is especially well suited for making stimulator connector tops or headers of epoxy electrically conductive. Other possible coating technologies are Physical Vapour Deposition, PVD, or Chemical Vapour Deposition, CVD, or any sputtering process.

It has been found that oxide layers, especially titanium oxide layers but also other metal oxide layers, may be found when such metals are used in the DC current environment dealt with in conjunction with the present invention. These oxide layers may cause an uneven current distribution which is detrimental to the infection control effect. The current may also be lowered due to increased impedance because of the oxide layer to a point at which the effect on bacteria in the biofilm is no longer effective. The formation of such oxide layers is avoided, according to an embodiment of the apparatus according to the invention, by coating the generator housing, and other metallic surfaces that may become oxidized due to the DC current, with one of the metals platinum, palladium or iridium or any other metal with similar electrochemical characteristics or an alloy of these metals.

In another embodiment of the apparatus according to the invention the counter electrode is an implantable electrode, suitably designed to be positioned on the lead for implantation into the patient's heart, preferably a heart stimulation electrode is forming said counter electrode. The need for a separate implanted counter electrode is then eliminated. In this case the electrical infection treatment has to be performed such that it does not interfere with stimulation pulses of the heart stimulator. Thus the treatment has to be restricted to the heart's refractory periods, or, alternatively, an infection treatment current of such a high frequency is used so that the heart is not affected.

In another embodiment of the apparatus according to the invention the counter electrode is formed by a large surface defibrillation electrode, said counter electrode can be designed for external application to the patient's skin, preferably formed by a patch electrode for external application to the patient's skin. By using large surface electrodes the current density will be lower and a uniform current distribution is more easily obtained. When using an external current source, which is natural particularly in the case of a counter electrode for external application, a galvanic connection is provided to connect the current source to implanted electrodes through the patient's skin.

In another embodiment of the apparatus according to the invention an inductive coupling arrangement is provided to inductively couple said externally located current source to said electrodes.

In another embodiment of the apparatus according to the invention the inductive coupling arrangement is a thin inductive coil attached to the outer surface of the pulse generator housing and electrically connected to the electrodes or an inductive coil positioned inside the pulse generator housing and electrically connected to the electrodes. Such thin coils, which are manufactured preferably by screen printing, will not require much space and will consequently contribute to a compact stimulator construction. Such a coil might also be used as a telemetry coil.

In a further embodiment of the apparatus according to the invention a rectifier is connected between the coil and one of the electrodes to supply a DC current to the electrodes.

In another embodiment of the apparatus according to the invention with the current source located externally, an electrolytic connection is provided for electrolytically connecting the current source to the first electrode. The electrolytic connector preferably is an additional electrode for external application to the patient's skin, separated from the counter electrode and in electrolytic contact with the first electrode, the current source being connected to the counter electrode and to the additional electrode. The biofluid of the patient's body can then serve as an electrolytic medium. In this way the great advantage of a non-invasive connection without transcutaneous wires is obtained. When using two external (patch) electrodes the current distribution on the housing and implanted electrode respectively might be non-uniform. This can be remedied, at least partly, by repositioning the external electrodes during the treatment, such that all implanted surfaces are coated by an adequate quantity of current.

The present invention also rebates to a heart stimulator having a pulse generator for delivering electric stimulation pulses to a patient's heart through a lead, connectable to the pulse generator, possibly through a connector top on a pulse generator housing, the pulse generator housing be electrically conductive and having an apparatus as disclosed above.

DESCRIPTION OF THE DRAWINGS

FIG. 3 schematically illustrates a heart stimulator in accordance with the invention with a surface-mounted coil on the exterior of the stimulator housing for inductively coupling an external current source to the infection current electrode.

FIG. 4 illustrates an embodiment of the invention with an external patch electrode forming the counter electrode.

DESCRIPTION OF THE PREFERRED EMBODIMENTS

Figure 1:
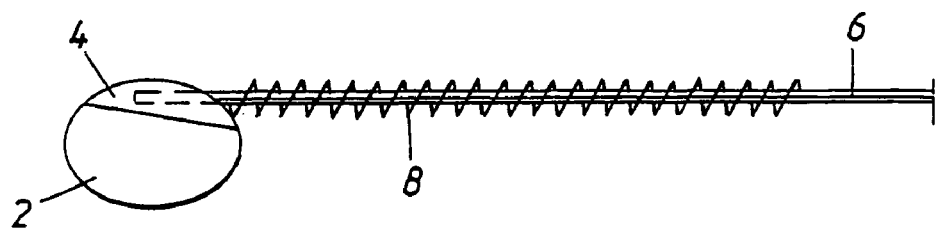
FIG. 1 schematically illustrates a heart stimulator with a lead having a coil on a proximal portion thereof, in accordance with the invention.

In the apparatus according to the invention the proximal part of the lead, extending to a position after implantation of the lead that is situated at a location beyond the entry into the venous system and before the entry into superior vena cava, is made electrically conductive. This can be accomplished in several different ways. Thus the proximal part can be made electrically conductive e.g. by applying an electrically conducting polymer on its surface or by ion implantation technology or Ion-Beam-Assisted-Deposition (IBAD). In FIG. 1 another example of making a proximal lead part electrically conductive is shown.

FIG. 1 shows schematically an implantable heart stimulator 2 having a connector top 4 to which a lead 6 is connected. The proximal part of the lead 6 is made electrically conductive by wrapping a metallic coil 8 around this part of the lead. The metallic coil 8 will also improve the wear resistance of the lead 6.

Figure 2:
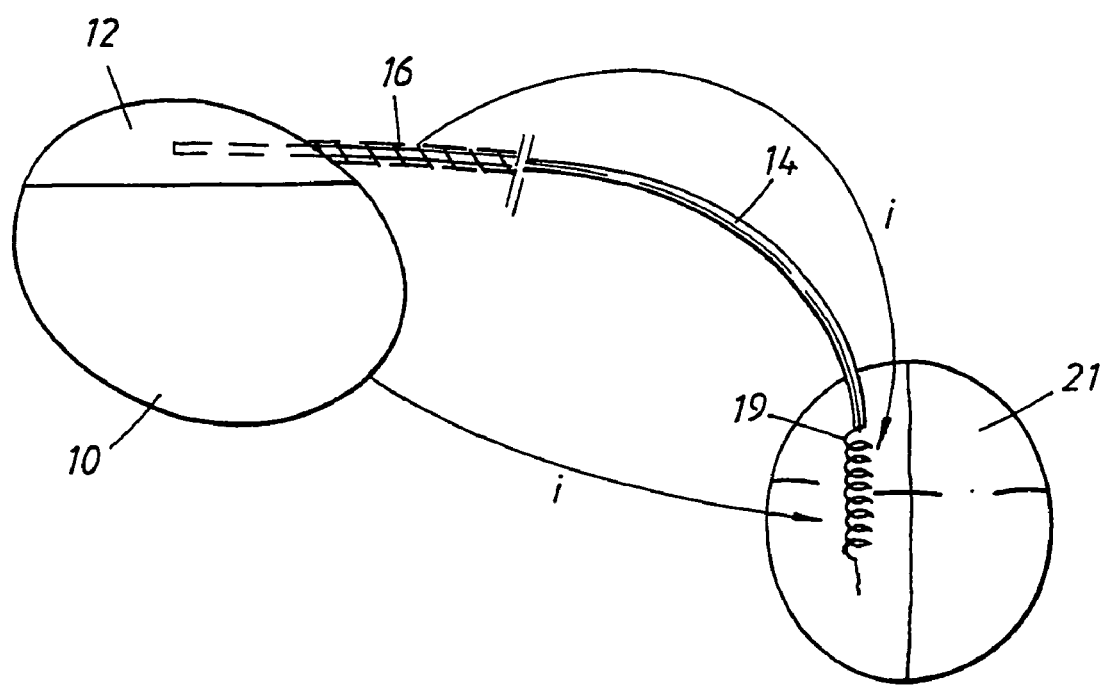
FIG. 2 illustrates an embodiment of the invention employing a large surface ventricular defibrillation electrode has the counter electrode.

The connector top or header 4 is often made of epoxy and IBAD is a suitable technique for making such a connector top conductive FIG. 2 shows an embodiment with electrically conductive exterior surfaces of the generator housing 10, the connector top 12 (header) and the proximal part 16 of the lead 14. The generator housing 10, the connector top 12 and the proximal part 16 of the lead 14 form one electrode, whereas a large surface right ventricular defibrillating electrode 19 on the lead 14 is used as a counter electrode. The pulse generator battery can be operable to deliver an infection control current i (treatment current) between this defibrillation electrode 19 and the electrode formed by the conductive housing 10, the connector top 12 and the proximal lead part 16 to destroy bacteria residing in a biofilm on the implanted stimulator. This infection control current i must not interfere with the stimulating function of the heart stimulator and is therefore delivered during the refractory period of the heart 21.

Other examples of implantable indifferent electrodes are disclosed in e.g. U.S. Pat. Nos. 5,510,766 and 5,814,076, these electrodes, however, being used for other purposes.

The electrical infection control requires a comparatively high amount of energy and therefore an external power source is normally needed. Transcutaneous electric connections to implanted electrodes increase the risk of recontamination of the wound and discomfort for the patient. It would therefore be a great advantage to use a non-invasive method for the energy supply.

FIG. 3 shows an example of supplying electric current for infection control from an external source by electromagnetic induction. Thus a super thin surface mounted coil 18 is attached to the exterior surface of the stimulator housing 20. This coil 18 can be manufactured by e.g. screen printing. A polymeric isolation film 22 is provided to electrically isolate the coil 18 from the stimulator housing 20.

One end 24 of the coil 18 is electrically connected to the housing 20, while the other end is connected to a diode 26 integrated in the epoxy connector head 28. The diode 26, in its turn, is connected to a counter electrode 31.

By applying a high frequency electromagnetic field by an external energy source located in the proximity of the stimulator, a current will be generated in the coil 18 by inductive coupling. The diode 26 will allow current to flow in only one direction for permitting the electrochemical processes necessary for the bioelectric effect to occur.

As an alternative, the coil can be implemented inside the stimulator housing. One end of the coil is then connected to the stimulator housing, whereas the other end of the coil is connected via a diode to an external counter electrode.

FIG. 4 shows an embodiment with the pulse generator housing 10, the connector top 112 and the proximal part 116 of the lead 114 forming one electrode, whereas an external patch electrode 122, intended for application on the patient's skin, is used as the counter electrode. In this case an external current source 124 is used for delivering treatment current i. When therapy had to be applied in this case, an electrically conductive needle 126, connected to the current source 124, is inserted through the patient's skin to make contact with a pulse generator housing 10. This embodiment has the advantage that only minor modifications of existing hardware are needed, viz. making connector top 112 and the outer surface of the proximal lead part 116 electrically conducting.

Numerous variations and modifications of the above described embodiments of galvanic connection as shown in FIG. 4 and inductive coupling of an externally located current source to implanted electrodes as exemplified in FIG. 3 are of course possible. As another alternative a connecting means can be used for electrolytically connecting an external current source to an implanted electrode. The electrolytic connecting means can be an additional electrode for external application to the patient's skin, separated from the counter electrode and in electrolytic contact with the first electrode via the body biofluid. By connecting the current source to the counter electrode and to this additional electrode a noninvasive method of connecting the current source is obtained.

When using external electrodes these electrodes preferably should be positioned such that those parts of the infection control current, which pass through the heart are minimized.

The invention claimed is:

1. An implantable heart stimulator comprising:
   a pulse generator, configured for implantation in a subcutaneous pocket, and an electrode lead connected thereto for delivering electrical stimulation pulses to a heart of a patient, said pulse generator having an electrically conductive housing;
   said electrode lead having a proximal portion which, after implantation of said electrode lead, extends substantially from the housing to a location situated beyond entry of the electrode lead into the venous system and before entry of the electrode lead into the superior vena cava, said proximal portion having an exterior with an electrically conductive surface;
   said housing comprising a connector header in which said electrode lead is mechanically and electrically connected, said connector header having an exterior with an electrically conductive surface forming, together with said housing and said conductive surface on the exterior of said proximal portion of said electrode lead, an infection control current electrode;
   a counter electrode disposed outside of said subcutaneous pocket; and
   a current source that supplies an infection control current between said infection control current electrode and said counter electrode that counteracts bacterial growth at least on an exterior of said housing.

2. An implantable heart stimulator as claimed in claim 1 wherein at least one of said electrically conductive surface on the exterior of said proximal portion of said electrode lead and said electrically conductive surface on said exterior of said connector header is formed by an electrically conducting polymer.

3. An implantable heart stimulator as claimed in claim 1 wherein at least one of said electrically conductive surface on the exterior of said proximal portion of said electrode lead and said electrically conductive surface on said exterior of said connector header is formed by an ion implantation.

4. An implantable heart stimulator as claimed in claim 1 wherein at least one of said electrically conductive surface on the exterior of said proximal portion of said electrode lead and said electrically conductive surface on said exterior of said connector header is formed by ion beam assisted deposition.

5. An implantable heart stimulator as claimed in claim 1 wherein at least one of said electrically conductive surface on the exterior of said proximal portion of said electrode lead and said electrically conductive surface on said exterior of said connector header is formed by a coating process selected from the group consisting of vapor deposition and sputtering.

6. An implantable heart stimulator as claimed in claim 1 wherein said electrically conductive surface on said exterior of said connector header is electrically isolated from said electrically conductive surface on said exterior of said proximal portion of said electrode lead.

7. An implantable heart stimulator as claimed in claim 1 wherein said conductive surface at the exterior of said proximal portion of said electrode lead is formed by an electrically conductive coil.

8. An implantable heart stimulator as claimed in claim 1 wherein said housing has an exterior coated with a metal selected from the group consisting of platinum, palladium, indium, platinum alloys, palladium alloys and indium alloys.

9. An implantable heart stimulator as claimed in claim 1 wherein said electrically conductive surface at said exterior of said proximal portion of said electrode lead is electrically isolated from said housing.

10. An implantable heart stimulator as claimed in claim 1 wherein said counter electrode is an implantable electrode.

11. An implantable heart stimulator as claimed in claim 10 wherein said counter electrode is carried by said electrode lead, adapted for implantation in the heart.

12. An implantable heart stimulator as claimed in claim 11 comprising a stimulation electrode, carried by said electrode lead for delivering said stimulation pulses, and wherein said counter electrode comprises said stimulation electrode.

13. An implantable heart stimulator as claimed in claim 1 wherein said counter electrode is a large surface area defibrillation electrode.

14. An implantable heart stimulator as claimed in claim 1 wherein said current source is an extracorporeal current source, and wherein said apparatus comprises an inductive coupling arrangement to inductively couple said extracorporeal current source with said housing and said electrically conductive surface on said exterior of said proximal portion of said electrode lead.

15. An implantable heart stimulator as claimed in claim 14 wherein said inductive coupling arrangement comprises a thin inductive coil attached at an outer surface of said housing, and electrically connected to said housing and to said electrically conductive surface on said exterior of said proximal portion of said electrode lead.

16. An implantable heart stimulator as claimed in claim 14 wherein said inductive coupling arrangement comprises a thin inductive coil disposed inside of said housing, and electrically connected to said housing and to said electrically conductive surface on said exterior of said proximal portion of said electrode lead.

17. An implantable heart stimulator as claimed in claim 14 wherein said inductive coupling arrangement includes a diode for producing a d.c. current as said infection control current.

18. An implantable heart stimulator as claimed in claim 1 wherein said counter electrode is adapted for external application to the skin of the patient.

19. An implantable heart stimulator as claimed in claim 18 wherein said counter electrode is a patch electrode.

20. An implantable heart stimulator as claimed in claim 18 wherein said current source is an extracorporeal current source, and further comprising a galvanic connection for electrically connecting said current source to said infection control current electrode.

21. An implantable heart stimulator as claimed in claim 18 wherein said current source is an extracorporeal current source, and further comprising a electrolytic connection for electrically connecting said current source to said infection control current electrode.

22. An implantable heart stimulator as claimed in claim 21 wherein said electrolytic connection comprises an additional electrode adapted for external application to the skin of the patient, separated from the counter electrode and in electrolytic contact with said infection control current electrode, said current source being connected to the counter electrode and to said additional electrode.

23. An implantable heart stimulator as claimed in claim 1 wherein said current source comprises a battery contained in said housing, which also supplies power to said pulse generator.

* * * * *